United States Patent [19]

Ramsey, III

[11] 4,360,029

[45] Nov. 23, 1982

[54] AUTOMATIC MEAN BLOOD PRESSURE READING DEVICE

[75] Inventor: Maynard Ramsey, III, Tampa, Fla.

[73] Assignee: Johnson & Johnson, New Brunswick, N.J.

[21] Appl. No.: 193,866

[22] Filed: Oct. 3, 1980

Related U.S. Application Data

[63] Continuation of Ser. No. 895,061, Apr. 10, 1978, abandoned, which is a continuation-in-part of Ser. No. 670,902, Mar. 26, 1976, abandoned.

[51] Int. Cl.$^3$ .............................................. A61B 5/02
[52] U.S. Cl. .................................... 128/681; 128/682
[58] Field of Search ................................ 128/680–683

[56] References Cited

U.S. PATENT DOCUMENTS

| | | | |
|---|---|---|---|
| 3,527,204 | 4/1970 | Lem et al. | 128/683 |
| 3,893,452 | 7/1975 | Birnbaum | 128/673 |
| 3,903,872 | 9/1975 | Link | 128/681 |
| 4,009,709 | 3/1977 | Link et al. | 128/681 |
| 4,074,711 | 2/1978 | Link et al. | 128/681 |

OTHER PUBLICATIONS

Geddes, L. A. et al., "*The Southwestern Veterinarian*", v. 23, Summer 1970, No. 4, pp. 289-294.
Posey, J. A. et al., *Cardiovascular Research Center Bulletin*, Jul.-Sep. 1969, v. 8, #1, pp. 15-25.

*Primary Examiner*—Kyle L. Howell
*Assistant Examiner*—Francis J. Jaworski
*Attorney, Agent, or Firm*—Audley A. Ciamporcero, Jr.

[57] ABSTRACT

An apparatus for producing information indicative of the mean blood pressure of a living creature through indirect measurement comprising an inflatable cuff, a pump connected to the cuff, a deflating valve connected to the cuff, measuring apparatus connected to the cuff adapted to measure cuff pressure and pressure oscillations occurring in the cuff caused by the heartbeat of the living creature and control apparatus connected to the pressure measuring apparatus, pump and deflating valve. Deflation of the cuff occurs in pressure increments, with processing being done at each given decrement to evaluate plural successive pulsations for purposes of artifact rejection and identification of a true pulsation.

11 Claims, 22 Drawing Figures

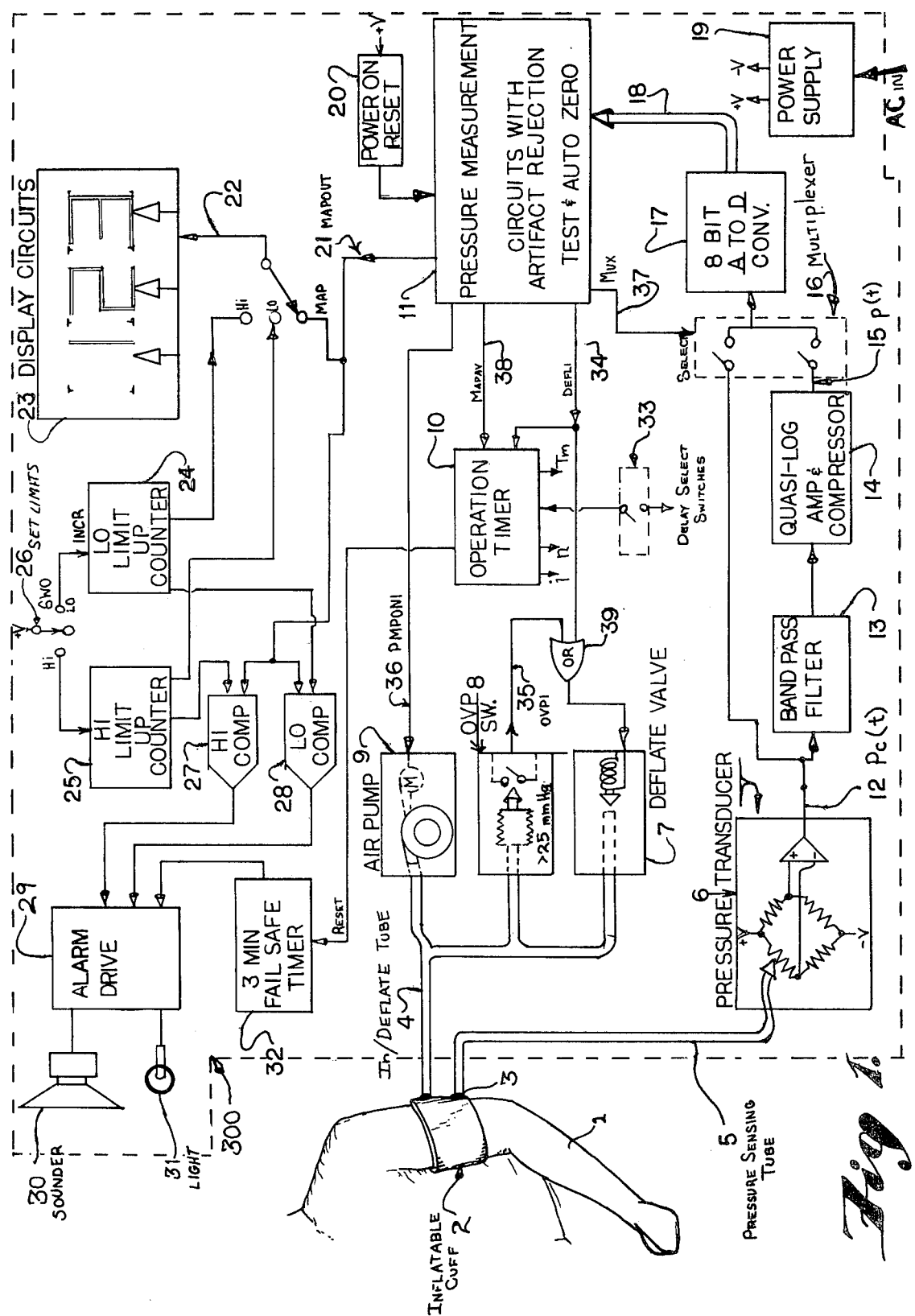

Fig 2.

| SYMBOL | T1 | T2 | T3 | T4 | T1 |
|---|---|---|---|---|---|
| NAME | PRE-MEASUREMENT | PUMP UP | MEASUREMENT | DELAY | (REPEAT) |
| Machine Activities or Condition | • Cuff deflated<br>• Previous Reading Displayed<br>• Auto-Transducer zero Circuits Enabled (within 11) | • Air Pumps 9, Enabled<br>• Adaptive Pump-Up Circuits Enabled (within 11) | • Pressure Determining Circuit 11 enabled; length of this interval is variable & depends upon Pressure Pulse Quality and Rate Measured<br>• New Pressure Measurement Displayed At End of Period on 23. | • Cuff Deflates<br>• No Activity<br>• Previous Reading Displayed<br>• Delay Period Set By Front Panel Switches (33) | |
| Approx. Duration | 7 sec. | 8 sec. | • About 30 sec. | 0.5 minutes to 8 minutes | |

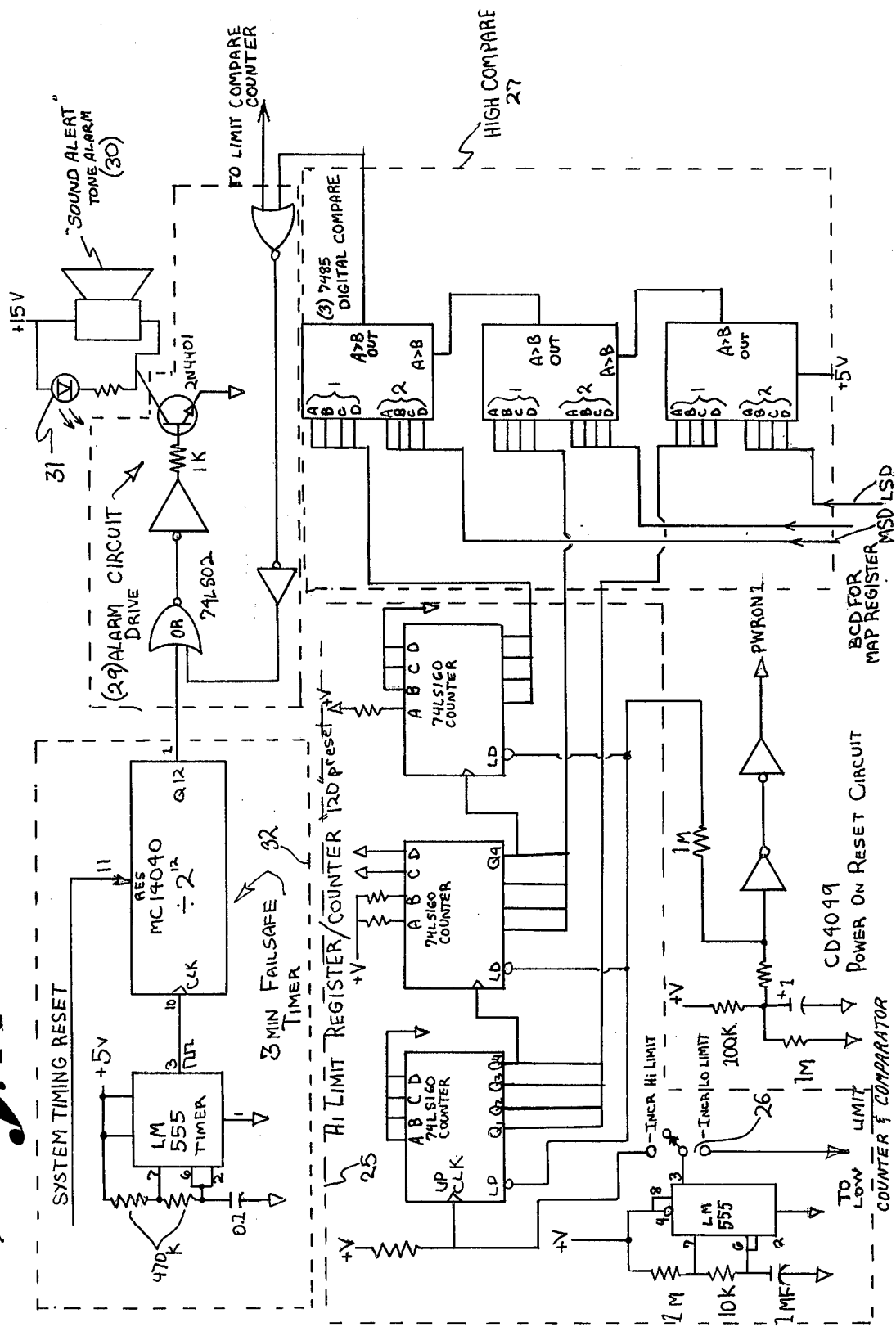

AUTOMATIC MEAN BLOOD PRESSURE READING DEVICE

This is a continuation of U.S. application Ser. No. 895,061, filed Apr. 10, 1978, now abandoned, which in turn is a continuation-in-part of U.S. application Ser. No. 670,902, filed Mar. 26, 1976, now abandoned. Reference is also had to U.S. application Ser. No. 136,129, a divisional of said abandoned continuation-in-part application Ser. No. 895,061.

BACKGROUND OF THE INVENTION

The invention generally relates to pressure indicating devices of the type used for the measurement of body fluid pressures and more particularly to an indirect non-invasive automatic mean blood pressure reading device.

FIELD OF THE INVENTION

The pressures of fluids in the vessels of all living things are indications of many facts which are of great value to those engaged in medical, biological and related fields. In the case of humans, the pressure in the vascular system is measured for many reasons, including diagnosis in pathology, laboratory routine for certain ailments, ascertainment of the progress of therapy, etc. As an example, the determination of venous blood pressure is an essential element in the diagnosis of a patient suspected of cardiac disease. Normal human venous blood pressure ranges between 80–120 millimeters water, whereas elevations of venous blood pressure above that range are found in cases of congestive heart failure.

True mean arterial pressure is not the arithmetic average of the systolic and diastolic pressure. Mean pressure depends on the amplitude and contour of the arterial pressure wave. Thus for example, if a person has a systolic pressure of 100 and a diastolic pressure of 50, the mean pressure would not be 75 but would be closer to 63 because the pulsation of the blood does not spend much time at the high systolic point as it retreats quickly from this peak pressure so that most of the pulsation time is spent at a lower pressure near the diastolic pressure. Thus if a total arterial wave form is ascertained, or its mean, a better picture of the patient's condition is presented to the physician. The presentation of only the systolic and diastolic pressure to a physician does not enable the physician to make a truly accurate assessment of the patient's arterial wave form. All that is really indicated by the pressure is that when the heart contracts, for some variable period of time the pressure in the artery goes up to systolic pressure. Thus the physician cannot determine if the pressure is for a tenth of a second, only that a particular pressure has been reached for some unknown instant. However, as to the actual pressure that the capillaries are encountering, the fluctuations are all, or practically all damped out. Thus by knowing the mean pressure the physician is better able to determine the pressure head that is driving blood through the capillaries.

Oscillatory mean blood pressure measurement is discussed in the "The Meaning of the Point of Maximum Oscillations in Cuff Pressure in the Indirect Measurement of Blood Pressure" July-September 1969, the Cardiovascular Research Center Bulletin page 15.

Presently the only means of measuring mean arterial pressure is to monitor it with direct intra-arterial means. While doctors are presently taking indirect measurements of the systolic and diastolic pressures of patients there is currently no automatic way that indirect mean blood pressure measurement can be obtained.

DESCRIPTION OF THE PRIOR ART

The most common method of obtaining indirect arterial blood pressure has been to gradually apply constructive pressure about the limb of the patient until the flow of blood through a vessel has been arrested, as determined by listening to a stethoscope applied over the vessel at a point distal the point of constriction. Then upon gradual release of the constricted pressure, the beginning of the flow through the vessel can be heard and the constricted pressure is noted on a gauge reading in millimeters of mercury. This pressure is referred to as systolic pressure. The pressure is then further gradually released until the sounds of the flow again cease and the pressure is again noted, which pressure is referred to as diastolic pressure. The difference between the diastolic pressure and systolic pressure is termed pulse pressure. Previous constriction pressure has been derived from an inflatable cuff connected to a mercury column manometer or to an aneroid type gauge having a dial scale calibrated in millimeters of mercury. While this common device is satisfactory for measuring the diastolic-systolic pressure range for a discrete period of time, it has the obvious disadvantage of not being able to continuously monitor the patient's blood pressure.

Many other attempts have been made to devise indirect blood pressure gauges which are portable, of reasonable cost and yet provide the attending physician with an accurate determination of the patient's blood pressure. One such device employs telescopically related, spring loaded tubes, the tubes being biased in an extended position. By exerting axial pressure on the tubes against an artery until blood flow in that artery is cut off, and by monitoring the relative displacement of the tubes from the fully extended position required to produce such flow cut off, the systolic pressure is monitored. However, this means for monitoring the displacement of the tubes is often inconvenient or clumsy.

Another prior art device employs a pointer extending from an inner tube through a longitudinal slot in an outer tube, the outer tube having calibrated markings adjacent the slot. A disadvantage with this arrangement lies in the fact that the tubes, and hence the pointer, return to the original biased position upon removal of the instrument from the body, thereby requiring the operator to take a reading while exerting direct pressure. Such a technique has been found to be inconvenient.

One automatic method which is used to obtain pressure readings comprises an ultrasound transducer which emits an ultrasound beam toward the artery. If the artery is pulsating, meaning that the pressure in the cuff is less than systolic pressure, it reflects back some of the ultrasound at a different frequency indicating that the pressure in the cuff must be below systolic pressure. Thus by starting the pressure of the cuff far above systolic pressure and bleeding it down slowly, one starts in a condition where the reflected ultrasonic sound is not of a changed frequency, that is the artery is not pulsating and as the cuff pressure bleeds down further at a certain point the artery will begin to pulsate which is indicated by a changed frequency. In the arterial pulsation method an ultrasound pickup or a microphone or stethoscope can be used. In whatever device is used, either ultrasound transducer or microphone, an instrument is utilized external to the cuff thus requiring a wire connecting the cuff to electronic circuitry used to make the pressure measurements.

There are several disadvantages in the above-mentioned types of devices, one being that in the microphone and stethoscope devices the turbulence in the flow of blood is heard rather than a change or a direct reflection of pressure. What the device relies on is that the pressure in the cuff occludes the flow of blood. Thus on the slow release of pressure the resumption of flow is difficult to determine in low flow state such as shock. In fact, in shock, the auscultatory method where one puts the microphone or stethoscope over the artery and listens to the flow fails because there is not enough flow to make Korotkoff noises. The ultrasound method works better than the auscultatory method in shock because it detects the movement of the artery rather than a flow within the artery. The disadvantages in the ultrasound device however, are that the external sensors must be closely and carefully applied over the artery and require a coupling jelly which can be messy. Even if the transducers are positioned very carefully, there is a possibility that they might shift during a lengthy operation, resulting in erroneous readings or no readings at all. Furthermore, the transducers are in an exposed position and can be easily broken resulting in expensive replacement costs.

In addition, with the ultrasound equipment, if one wants to measure the blood pressure of a child, a different size transducer must be used from the transducer used to measure the blood pressure of an adult necessitating the change of the transducer besides the additional cost of purchasing the different size transducer.

Another indirect measuring device is shown in U.S. Pat. No. 3,903,872 which teaches a system for measuring systolic and diastolic pressure by using a blood pressure cuff with a transducer mounted on the outside of it. The cuff is linearly inflated from zero pressure and during inflation the device picks for diastolic pressure the cuff pressure at which the slope of the first derivative just before the onset of a beat was a negative maximum and chooses for systolic pressure a point of the cuff pressure at which the second derivative was maximum.

Another indirect measuring method measures oscillation in the cuff pressure. The method dates from the turn of the century but has not been widely utilized because of the problems associated with it. It should be noted that the indirect measurement of mean blood pressure in a horse has been taken with the use of an oscillometer and a physiograph. This indirect measurement is described in The Southwestern Veterinarian, Volume 23 Summer of 1970, number 4 pages 289-294 and appears to be the most pertinent reference known to applicant in relation to the present invention. In this publication the cuff pressure was recorded on the physiograph and the oscillations in cuff pressure were amplified and displayed by a rapid responding meter on an electronic oscillometer with the amplified oscillations being recorded on the physiograph along with the direct arterial pressures. This method of measuring mean pressure requires operator judgment as to when the oscillations are maximum, which is difficult to quickly and correctly ascertain.

SUMMARY OF THE INVENTION

The present invention relates to automatic indirect blood pressure reading apparatus that automatically and adaptively pumps up an arm cuff to a proper pressure by taking the previous cuff pressure measurement and adding approximately 60 mm of mercury to the old pressure before beginning measurement of the amplitude of the oscillations in the cuff.

This adaptive pump-up feature minimizes the period of time that blood flow is occluded in the arm by minimizing the amount of overpressure required to occlude.

Once the amplitude of the oscillations at the starting pressure are measured the cuff is deflated a pre-determined pressure increment to a lower pressure and the oscillations at this lower cuff pressure are then measured. It is required that the pressure oscillations satisfy a plurality of artifact detecting tests before a peak to peak oscillation measurement is accepted as valid. Should an artifact be detected, additional oscillations are measured until the oscillations are tested to be free of artifacts. When this integrity test is satisfied or some predetermined time interval is exceeded, the cuff is once again deflated a pressure increment. The apparatus continues in this fashion until maximum amplitude oscillations are obtained at the lowest cuff pressure which is indicative of the mean arterial pressure. If after several deflation cycles after the maximum oscillation is reached and no peak to peak oscillation value is found which is greater than the peak to peak value which was previously ascertained, the cuff pressure at which the oscillations were maximum is displayed as mean arterial pressure and the cuff is purged to allow the venous blood trapped in the arm to drain. A programmed wait cycle is then entered and the entire procedure is repeated at the end of the wait period.

The invention is an indirect and non-invasive automatic device that pumps a cuff up and measures the mean blood pressure value automatically as it automatically deflates in pressure increments without any operator intervention. Additionally, it can be made to display a number proportional to the magnitude of peripheral pulsation which can be useful in determining the amount of vasoconstriction.

Measurement of mean arterial pressure by means of incremental deflation, conditioned upon successfully passing a plurality of oscillation integrity tests, forms a novel aspect of this invention and a desirable structure to satisfactorily operate reliably without human intervention.

The invention is constructed with a pressure transducer, air-pump, deflate valve, and a plurality of linear and digital semiconductor integrated circuits positioned within a cabinet enclosure. A three digit, numerical display indicates mean arterial pressure and an accessory printer can be used to print a tape for a permanent record.

The above mentioned purposes and operation are more readily apparent when read in conjunction with the following detailed description of a preferred embodiment of the present invention.

BRIEF DESCRIPTION OF THE DRAWINGS

FIG. 1 is a schematic block diagram of the overall invention.

FIG. 2 is a timing diagram of the cyclic action taken by the invention when performing mean arterial pressure measurements automatically.

FIG. 11 is an electronic schematic showing implementation of a typical sub-system of the invention using standard commonly available linear and logic semiconductor circuit components.

DESCRIPTION OF THE PREFERRED EMBODIMENT

Figure 3:
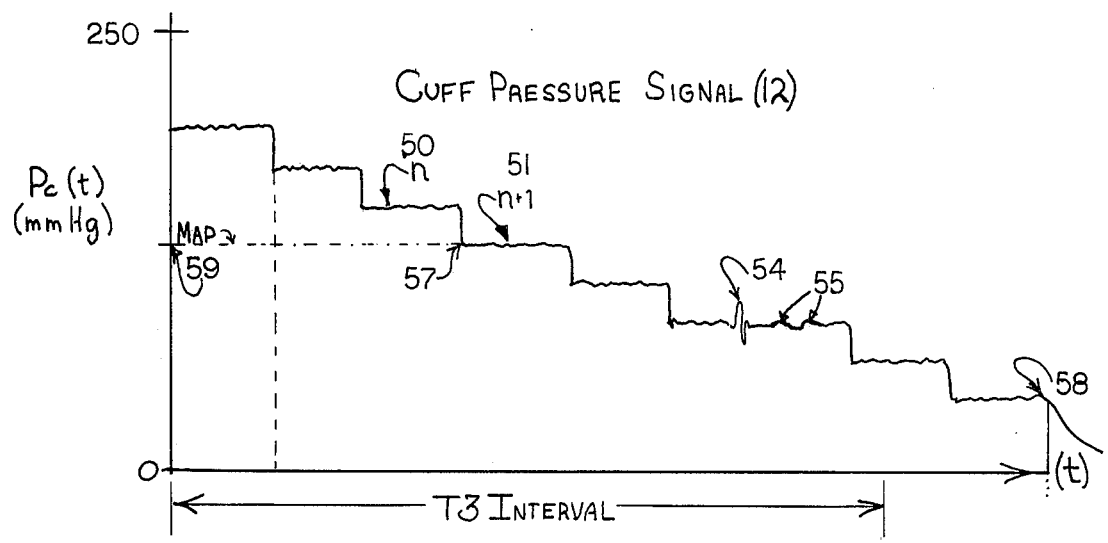
FIG. 3A is a timing diagram of the applied cuff pressure signal during measurement.
FIG. 3B is a timing diagram of the arterial pulse pressure signal during measurement.
Figure 3:
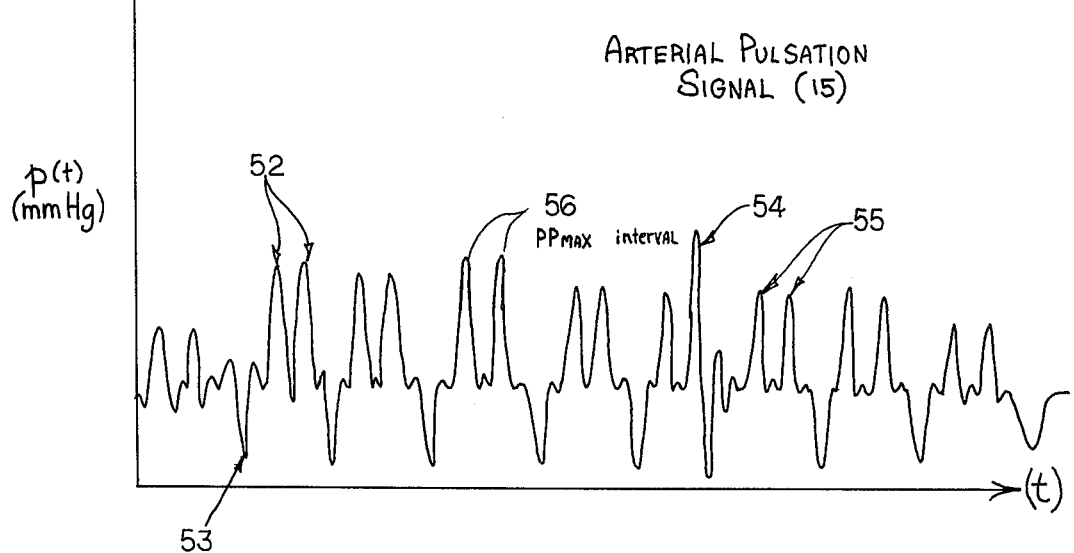

The automatic mean arterial blood pressure measuring apparatus as shown in FIG. 1 basically consists of an inflatable cuff 2 wrapped around an arm 1, pump up and deflation means 7 and 9, and electronic pressure measurement apparatus 6, 10, 11, 13, 14, 16 and 17 with numeric display means 23. With the exception of the cuff all the component parts are housed within cabinet 300. Additional circuits are provided to alert attending personnel to abnormal pressure or operating conditions. Further patient safety is enhanced with a protective overpressure switch 8 which will cause cuff deflation should the pump fail to shut off in a normal, controlled manner. The novelty of this invention primarily resides within the pressure measurement circuits 11 combined with conditional, incremental cuff deflation by means of deflate valve 7.

In operation, cuff 2 is wrapped around arm 1 and is automatically inflated to a predetermined pressure via air-tube 4 by air-pump 9. A pressure sensing tube 5 is connected to cuff 2 at point 3 and is coupled to an electronic pressure transducer 6. This transducer outputs a voltage proportional to the air pressure of tube 5 which typically consists of a d.c. voltage with a small superimposed, variational component which is caused by the arterial blood pressure pulsations in arm 1.

The transducer 6 produces an output 12 which is routed to a multiplexer 16 and to a bandpass filter 13 which in turn is connected to a quasi-logarithmic amplifier and compressor 14, having an output signal 15 to multiplexer 16. Subsystems 13 and 14, namely the filter and amplifier are designed to reject the d.c. component of pressure signal 12 and yet amplify the blood pressure pulsations. The filter 13 passes those signals whose frequency components lie in a range from 1 to 10 Hz and strongly rejects other frequency components. Amplifier 14 magnifies low level signals from filter 13 and reduces the level of larger signals in a manner approximating that of a logarithmic curve. These components are not novel and are readily implemented by one skilled in the art. The cuff pressure signal 12 and pressure pulsation signal 15 will be further described in the discussion of FIG. 3.

The multiplexer 16 selects one of two pressure signals and inputs it into a sampling analog to digital convertor 17. Each sampled pressure point is represented by 8 binary bits which are routed via line 18 to pressure measurement circuits 11.

Circuits 11 employ a plurality of logic circuits to determine the minimum cuff pressure for which a maximum pulsation exists. This cuff pressure produces a signal output on connection 21 to display 23. Circuits 11 also transmit a deflate control signal 34 to valve 7 via OR gate 39, a multiplexer select signal 37 and a control signal 38 indicating to apparatus timer 10 that a mean arterial pressure measurement is complete. Also a power-on reset signal is transmitted from 20 to properly initiate logic states when power from supply 19 is first turned on. Detailed circuit operation of 11 will be described later.

As shown in FIG. 1, the MAPOUT signal 21 is also routed to comparators 27, 28 where the value is compared to the patient pre-determined acceptable pressure limits as stored in counter/registers 24, 25 and found within those limits. These limit values are set to desired values by switch 26 which causes the counters to up-count in steps of 5 mmHg. The stored limit value is displayed by switch 22 which connects the display to either the high or low limit registers. Should the measured means arterial pressure be below the predetermined low-limit, then comparator 28 activates alarm circuits 29 which generate an audible tone with sounder 30 and a visible flashing light with light 31.

Another output signal transmitted from the measurement circuits 11 is the MAPAV signal 38. This "mean-arterial-pressure-available" signal indicates to the system operation timer 10 that a measurement is complete, and that the timer may sequence to its next operation.

The operation timer 10 controls overall apparatus timing and is built with conventional, logic integrated semiconductor circuits. It is constructed with a crystal oscillator for precise timing and generates a plurality of timing control signals. Output pulse "i" is the basic sampling pulse and causes the A to D convertor 17 to take uniformly spaced samples. Output pulse "n" exists each time a new pressure increment interval is to be measured. The output pulse "n" is used by counting circuits in 11. Timing signals "Tm" generated from timer 10 are used by the apparatus to operate each separate operation and are shown in FIG. 2.

FIG. 2 is a diagram defining and summarizing each of four operation timing intervals. T1 is the premeasurement interval lasting about 7 sec. in which cuff 2 is stably deflated while display 23 continues to display the last MAP reading. Circuits within 11 are enabled to automatically zero the transducer 6 in case it has drifted. A detailed description of this circuit will be given later.

T2 is the interval in which the air-pump 9 inflates cuff 2 to a value which is adaptively set. The circuits and their operation for ascertaining this value will be described later. The pump-up time is typically 5 sec.

Apparatus alarms 29, 30 and 31 are also used to alert attending personnel to a possible failure. Should the sampling pulse "i" fail or MAPAV fail to give a reading after 3 minutes, then the failsafe alarm 32 will activate the alarms.

Operation timer 10, also has a control input from delay select switches 33 which are user selected for the desired interval between automatic measurements.

T3, in FIG. 2, is the interval during which the cuff 2 is incrementally deflated by valve 7 under control of the pressure measurement circuits 11. The exact duration of this interval is dependent upon the quality of the measured arterial heart pressure pulses. For example, if the patient should be moving his arm or the attending surgeon should be bumping against the cuff 2, then the artifact sensing circuits in 11 will reject the affected pulsations and cease further cuff deflations until apparently good pulsations are detected. Thus, the typical T3 interval is about 30 sec. but could extend to over a minute. Once circuit 11 has completed its measurement, the MAPAV signal 38 advances the timer to interval T4, and the new MAP is displayed on 23.

Interval T4 initiates cuff deflation and is followed by a period of apparatus inactivity. The cuff is emptied quickly to minimize patient discomfort. This idle interval is user settable with delay switches 33 for 0.5 to 8 minutes.

After interval T4, the apparatus repeats the described operations starting again with interval T1.

A detailed description of the measurement circuits 11 requires some definition of the basic pressure signals 12 and 15 (FIG. 1). Reference is now made to FIG. 3A and 3B which shows typical behavior of the cuff-pressure signal Pc(t) and the arterial pulsation signal p(t). During a measurement interval, the cuff pressure is incrementally decreased causing cuff pressure signal voltage 12 to proportionately decrease. Each step n(50) and its successor (n+1) (51) is about 5 mmHg less. The arterial pulsation signal 15 shows each pulse 52. This signal also shows the deflate transient 53 which is ignored by logic in circuit 11 as will be later described. Also shown is an artifact pulse 54 as might be caused by someone hitting the cuff. Note that additional pulses 55 are measured before another deflate is initiated. Arterial pulse pair 56 would be decided by measurement logic circuits 11 to be the maximum peak-to-peak arterial pulses according to circuits to be described. The corresponding cuff pressure 57 would be decided to be the MAP 59 and displayed on display 23. Once 5 deflations have been made beyond pulse point 56 or the cuff pressure 12 is less than 20 mmHg., the cuff is deflated. This is shown as point 58 on the cuff pressure signal.

Figure 4A:
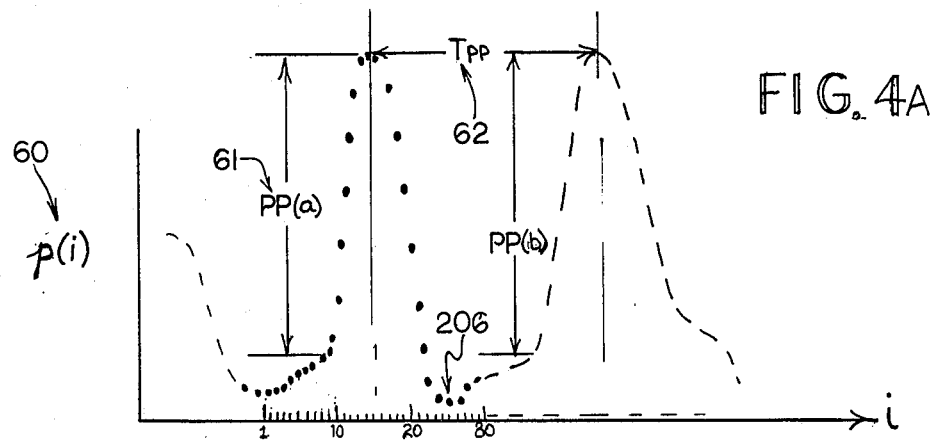
FIG. 4A is a signal characteristic diagram showing a time sampled arterial pulsation signal.
Figure 4B:
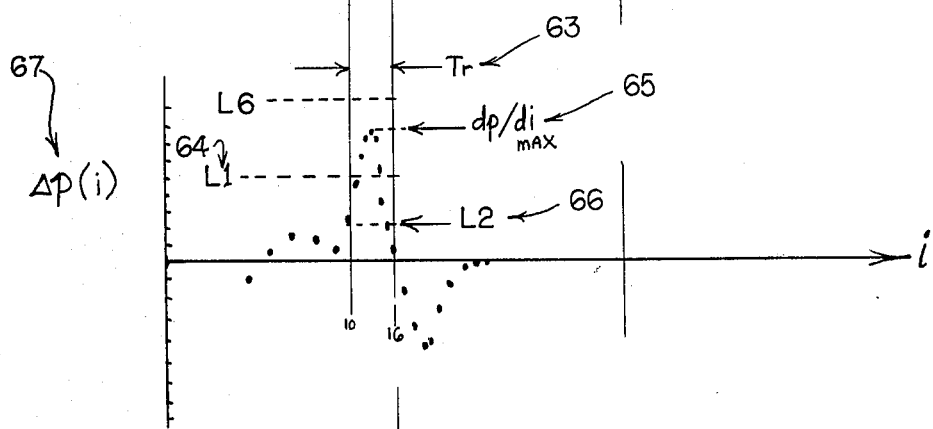
FIG. 4B is a signal characteristic diagram showing the derivative of the signal of FIG. 4A.
Figure 4C:
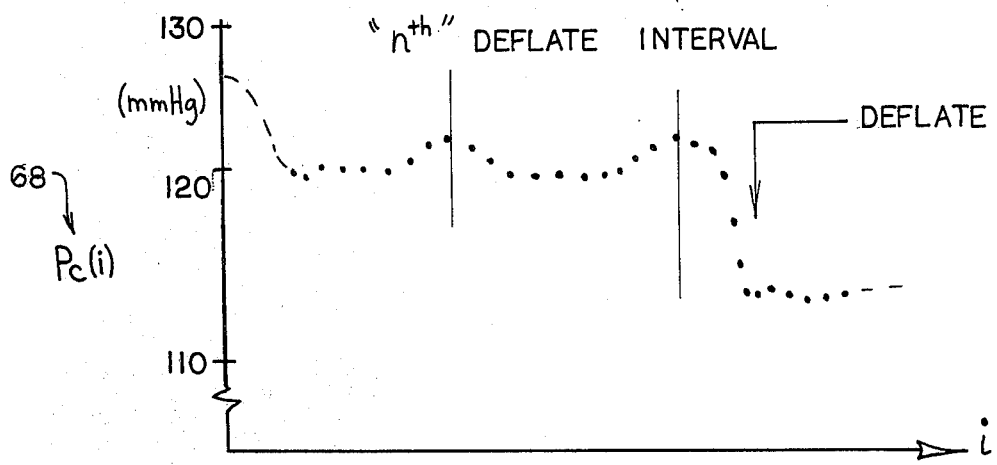
FIG. 4C is a signal characteristic diagram of a sampled cuff pressure signal taken simultaneously with the signals of FIGS. 4A and 4B.

The cuff and arterial pressure signals 12, 15, are digitized by convertor 17 and analyzed by circuits 11 (FIG. 1). Certain important digitized signal characteristics are shown in FIG. 4. The sampled arterial pulse waveform p(i), 60, has three important characteristics: 61 is its peak to peak value PP(n) where n is the number of the current deflate interval; 62 is the duration between pulse peaks, Tpp, expressed in number of clock samples, i; and 63 is the pulse rise time, Tr, also expressed as a number of clock samples. These characteristics are derived by circuits in 11 with aid of the signal derivative waveform 67. Details of this waveform (64, 65, 66) will be described later.

The corresponding typical sampled cuff pressure signal 68 is also shown, and is used by a plurality of circuits in 11 in a manner which will be described.

Figure 5:
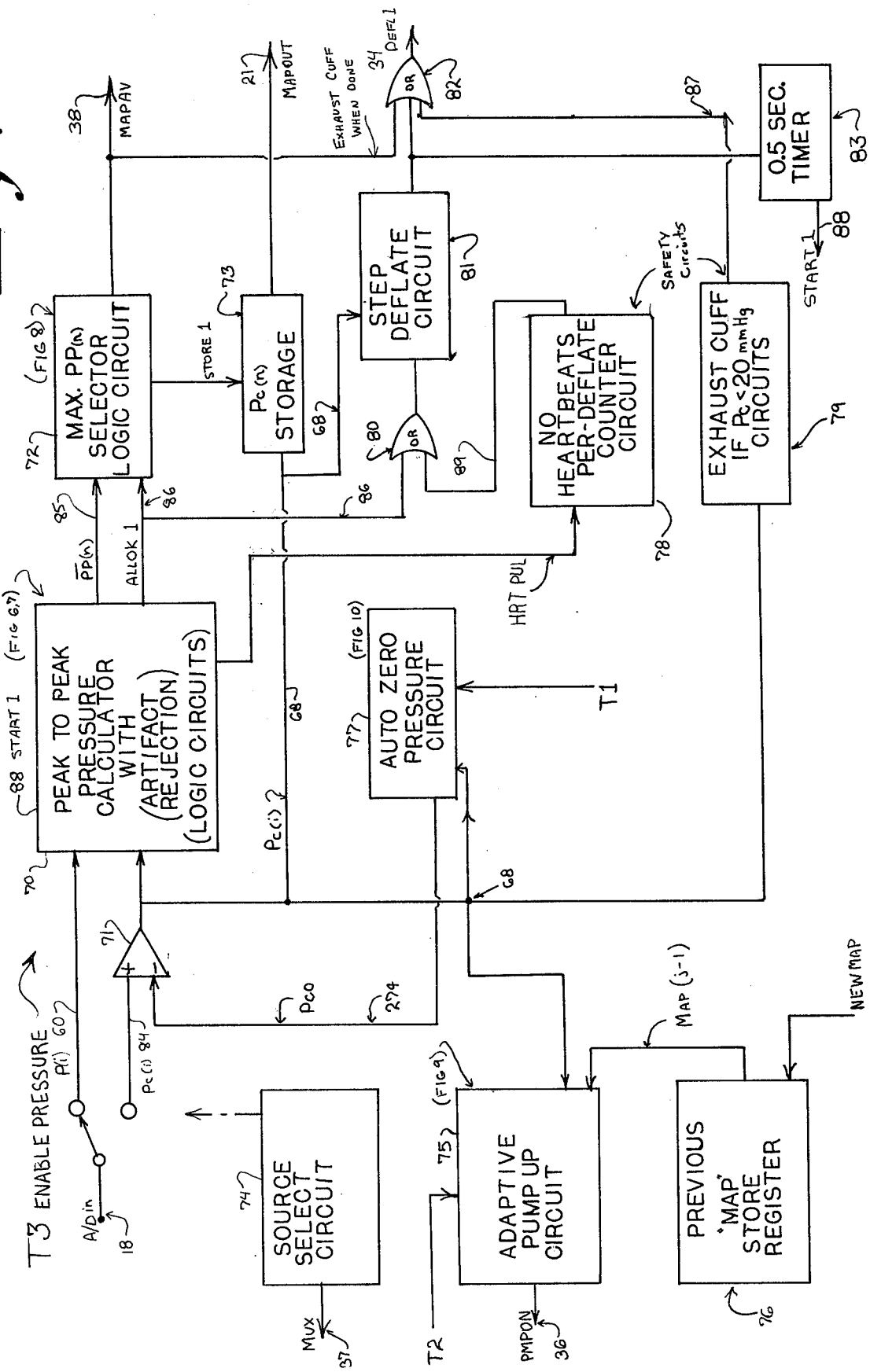
FIG. 5 is a schematic block diagram of the pressure measurement circuits shown in FIG. 1.

An expanded functional diagram of all the circuits contained within the pressure measurement subsystem 11 is shown in FIG. 5. Most of these circuit blocks will be further expanded to the detailed operating circuit level in FIGS. 6 through 9.

The pressure measurement circuits subsystem contains circuits which are operational during three timing intervals. During, T1, circuits 71 and 77 are activated to accomplish pressure transducer autozeroing. Basically, source select circuit 74 connects the A to D signal 18 to differencing amplifier 71 which transmits an output signal showing the difference between a previously stored auto-zero pressure (Pco) and the new presumed zero cuff pressure, Pc'(i) 84. Pco is adjusted by circuit 10 to force Pc(i) 68 to be zero value in a manner to be described later. This "new" Pco value is retained throughout the following T2, T3, and T4 intervals.

During interval T2, adaptive pump-up circuits 75 and 76 are activated and line 18 is connected to 71. If a previous MAP value exists in storage register 76, then circuits 75 enable the pump via line PMPON 36 to pump until the cuff pressure is 60 mmHg over this previous MAP value. The details of this will be discussed later on in the specification. When the desired cuff pressure has been achieved as determined by measuring the pressure on signal line 68, then the next timing cycle T3 is entered.

Signal T3 activates all of the measurement circuits during this interval consisting of circuits 70, 71, 72, 73, 80, 81, 82 and 83. Heartbeat counter circuit 78 and cuff exhaust circuit 79 are ancillary safety circuits. The basic operation of these circuits is as follows.

Circuit 70 calculates the average peak to peak value of the first two arterial pulses in which no artifacts have been found. When the artifact checks are found to be "all-okay" then the control line 86 sends the average peak to peak pulse value to max. selector circuit 72. This circuit, in turn, causes circuit 73 to store the corresponding cuff pressure 68, if no previous stored peak-to-peak value was larger. On the first step, the prestored value is always zero. The "all-okay" signal also initiates a step deflate in cuff pressure via line 90 through gate 80 to step-deflate circuit 81. Circuit 81 deflates cuff 2 via OR gate 82 with control line 34 to a value 5 mmHg less pressure. The correct pressure is measured with line 68. The timer 83 generates a "start" pulse 88 one-half second after step deflate circuit 81 stops deflating as determined via line 87, which delay permits the cuff pressure transient 53 (FIG. 3B) to die away before starting another peak to peak measurement in 70. Start pulse 88 initiates another measurement cycle at the lower cuff pressure. This process continues until circuit 72 determines that it has successfully selected the minimum cuff pressure in 73 for which the average peak to peak pulsations 85 were a maximum. The details of this selection are discussed later in the specification. The Mean Arte rial Pressure Available signal 38 is transmitted to the operation timer 10, which advances the timer to state T4. Simultaneously, the "MAP OUT" signal 21 is sent to the display.

Safety circuit 78 is a simple logic counter which determines if the number of heart pulses is in excess of fifteen during any pressure step which only happens if no pulse pair is free of artifacts. Its output signal, 89, initiates another cuff deflate via OR gate 80. By limiting the maximum time the cuff pressure may dwell on any one increment, undue patient discomfort is avoided.

The other safety circuit, 79, senses when cuff pressure has reached a useful minimum of 20 mmHg pressure and then initiates a full cuff deflate via gate 82.

Figure 6:
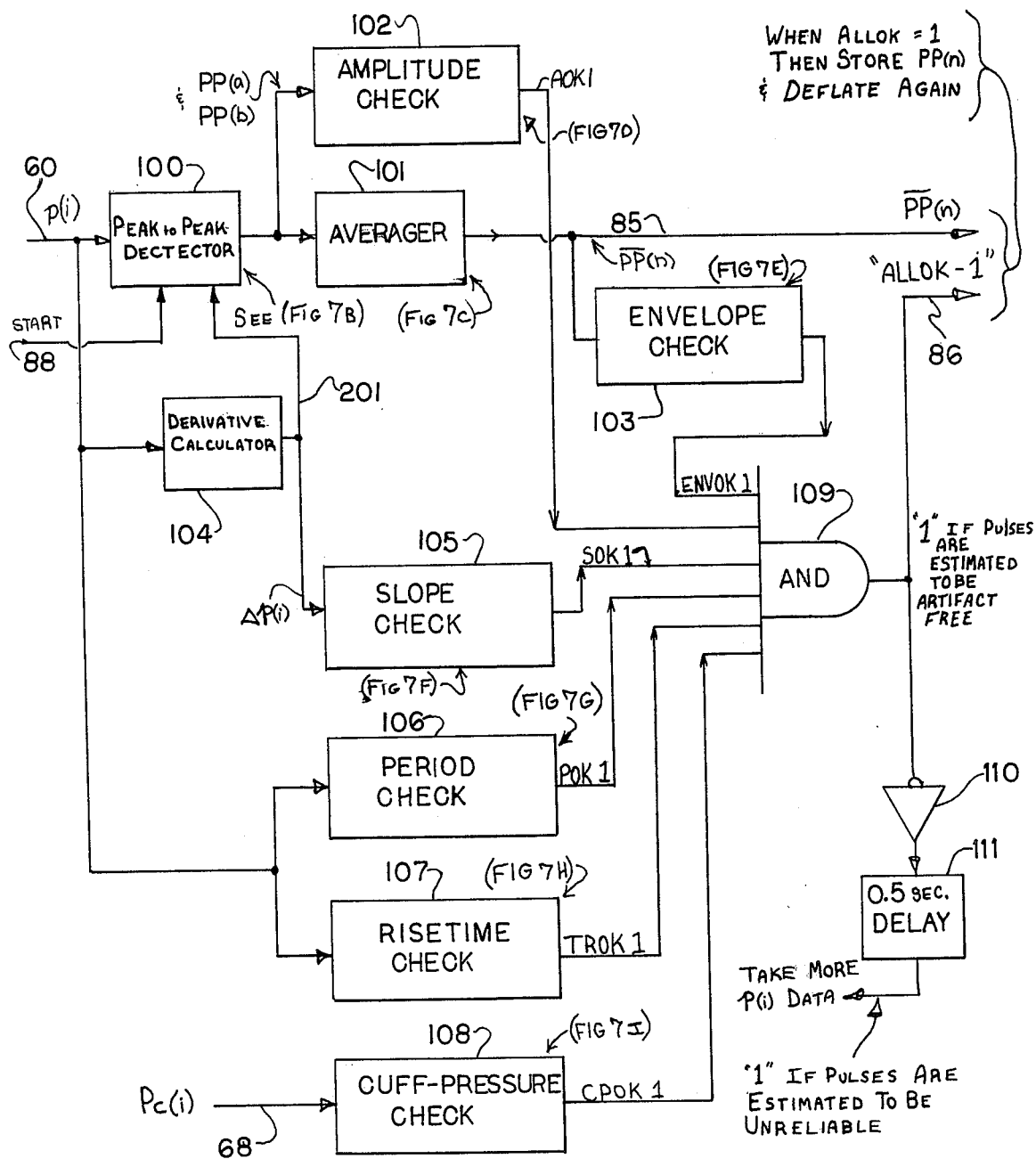
FIG. 6 discloses a block diagram of the peak to peak calculator with artifact rejection circuits shown in FIG. 5.

An important and novel feature of this invention is the incorporation of sophisticated artifact detection circuits which are incorporated in pressure calculator 70 and shown in more detail in FIG. 6. The peak to peak calculator consists of circuits 100, 101, and 104. Peak to peak detector 100 determines the difference in value between the pulse maximum and base of the pulse wave form where the positive slope first exceeds a predetermined threshold as was shown in FIG. 4. This value is found for two successive arterial pulses and averaged by circuit 101. This average peak to peak value $\overline{PP}(n)$ is transmitted on line 85.

Artifact detection circuits 102, 103, 105, 106, 107 and 108 have their signal outputs AND'ed by gate 109. Only if all of these circuits are satisfied to be artifact free is the "All-okay" line 86 enabled on this subsystem output. Should an artifact be detected, inverter circuit 101 enables 0.5 second timer 111, which in turn causes all of the peak to peak calculator circuits to take additional pulse pair measurements without another cuff deflate. The 0.5 second delay gives time for the artifact transients to die out in the pneumatic system (2,4,5,6). The peak to peak calculator and artifact rejection circuits as described in FIG. 6 are seen to embody three principles vital to the reliable determination of non-invasive mean arterial blood pressure by automatic means: (1) determining peak to peak heart pulse value by analysis of its time derivative (described in detail in FIGS. 7A and 7B), (2) performing an average operation on a plurality of arterial pulses (described in detail in FIG. 7C), and (3) not permitting another incremental cuff deflation until at least a pair of heart pulses successfully pass a plurality of artifact sensing tests. These artifact sensing tests are described in detail in FIGS. 7D, E, F, G, H, and I.

The time derivative of the heart pulse signal p(i) is calculated to aid the peak to peak detector and artifact sensing circuits. The derivative calculator 104 is shown in detail in FIG. 7A. The detail shown in this figure and the remaining figures is sufficiently detailed so that they are readily implementable with commercially available logic circuits by one skilled in the art of electronics design. The derivative calculator 104 simply calculates the difference between the current pressure pulse value 6 and its previous value. The difference is transmitted as an output signal as the derivative 201.

Figure 7A:
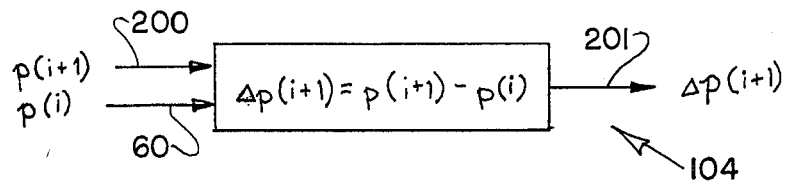
FIG. 7A discloses the circuit operation of the pressure derivative calculator of FIG. 6.
Figure 7B:
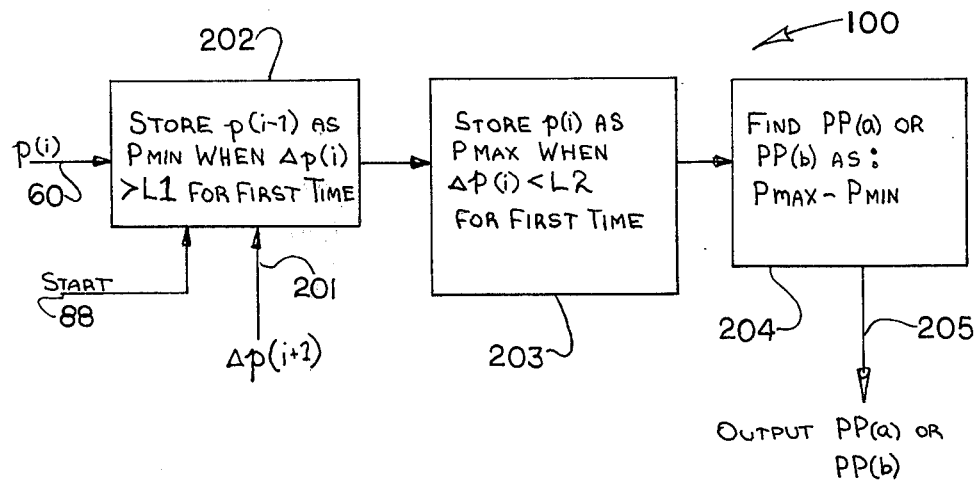
FIG. 7B discloses the circuit operation of the peak-to peak detector of FIG. 6.

This value is used by peak to peak detector 100 as shown in FIG. 7B. The first circuit 202, compares the derivative 201 to a predetermined value "L1". When L1 is exceeded in value by 201, then the previous pressure sample p(i-1) is stored as the minimum value of the heart pressure pulse "Pmin." The maximum value of the pulse is then determined as the p(i) value where the derivative is below a threshold value "L2" which is near zero. The corresponding p(i) value is stored as Pmax by circuit 203. Circuit 204 calculates the peak to peak value as Pmax-Pmin and outputs it as signal 205, PP(a). A second pulse is similarly found, PP(b), and transmitted on line 205 to averager circuit 101. The relative relationship of thresholds L1 and L2 are easily seen in FIG. 4B. The important and novel feature about this peak to peak calculation is that the minimum of the pulse is measured at the base of the heart systolic pulse rather than the diastolic transient minimum (see FIG. 4B, 206). This technique has been found to yield more accurate MAP measurements with less variance when compared to direct, invasive pressure measurements.

Figure 7C:
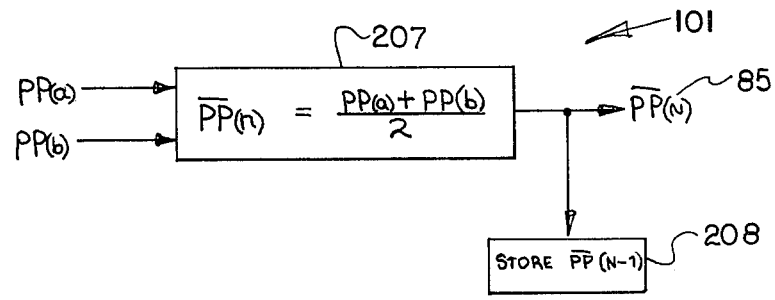
FIG. 7C discloses the circuit operation of the averager of FIG. 6.

Averaging circuit 101 as shown in FIG. 7C sums PP(a) and PP(b) and divides them by 2. The previous value is stored in register 208 and the new average is transmitted as output signal 85. The averager circuit provides immunity to high frequency, low-level pressure artifacts.

Figure 7D:
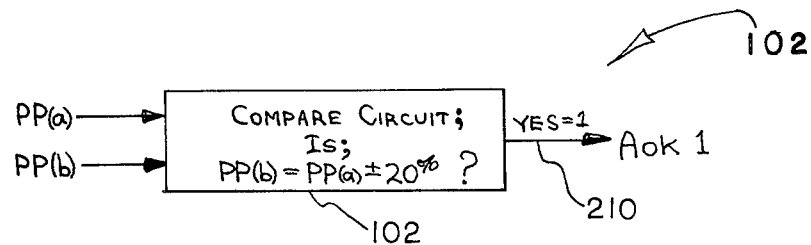
FIG. 7D discloses the circuit operation of the amplitude check of FIG. 6.

The amplitude check circuit 102 is shown in FIG. 7D. The two adjacent peak to peak values PP(a), PP(b) output signals by the peak to peak detector 100 are compared in amplitude. If the second value differs by less than 20% of the first value, then the check is satisfactory and a binary signal output one is transmitted; otherwise the output is a binary zero. Circuit 102 is effective at detecting pressure artifacts such as attending personnel hitting the cuff accidentally in synchronism with the arterial pulses.

The purpose of this tolerance requirement is to reject those beats which are widely variable in amplitude from beat to beat such as could be caused by premature ventricular contractions. Not only does this eliminate the acceptance of variable data during heartbeat irregularities but it also is quite useful for reducing the influence of pulsation artifacts caused by subject motion or outside interference such as the physician bumping against the cuff as could occur in an operation.

Figure 7E:
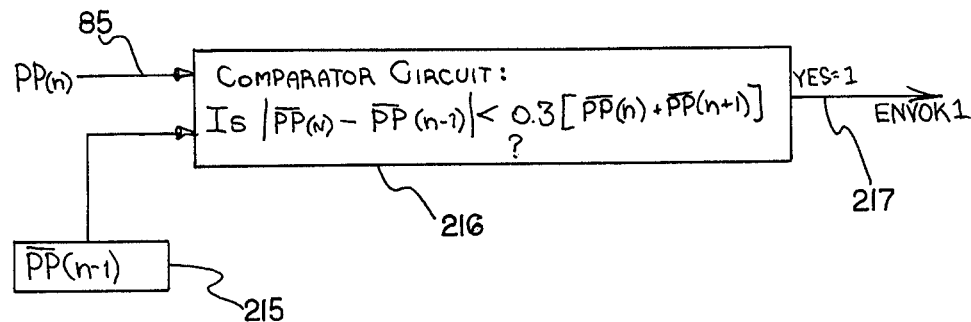
FIG. 7E discloses the circuit operation of the envelope check of FIG. 6.

Should two artifact pressure pulses be caused of approximately the same amplitude, such that it would satisfy the test of circuit 102, another amplitude test is made by circuit 103 shown in detail in FIG. 7E. This circuit compares the envelope, that is, the calculated average peak to peak heart pulses $\overline{PP}(n)$, 85, with the previously calculated value of the previous cuff pressure increment. As shown in FIG. 7E, the absolute difference of these average peak to peak values must be less than 30% of their sum to pass the test. As was shown earlier in FIG. 3, the heart pressure peak to peak amplitudes change gradually between cuff deflation increments and the comparator 216 and register 215 of circuit 103 will detect violations of this rule.

Figure 7F:
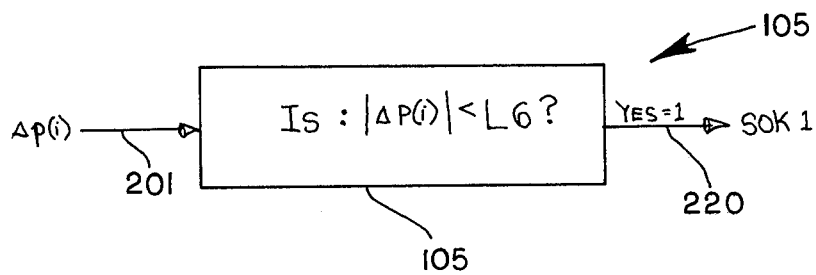
FIG. 7F discloses the circuit operation of the slope check of FIG. 6.

Another artifact detecting circuit 105, FIG. 7F, determines if the heart pulse derivative 201 ever exceeds a predetermined limit L6. Since the human heart cannot increase arterial pressure faster than some maximum, this circuit tests to see if that maximum is exceeded due to any artifact. If this test is passed, output signal 220 is a binary one. Otherwise it is a binary zero. The relative value of this limit L6 is shown in FIG. 4B.

Figure 7G:
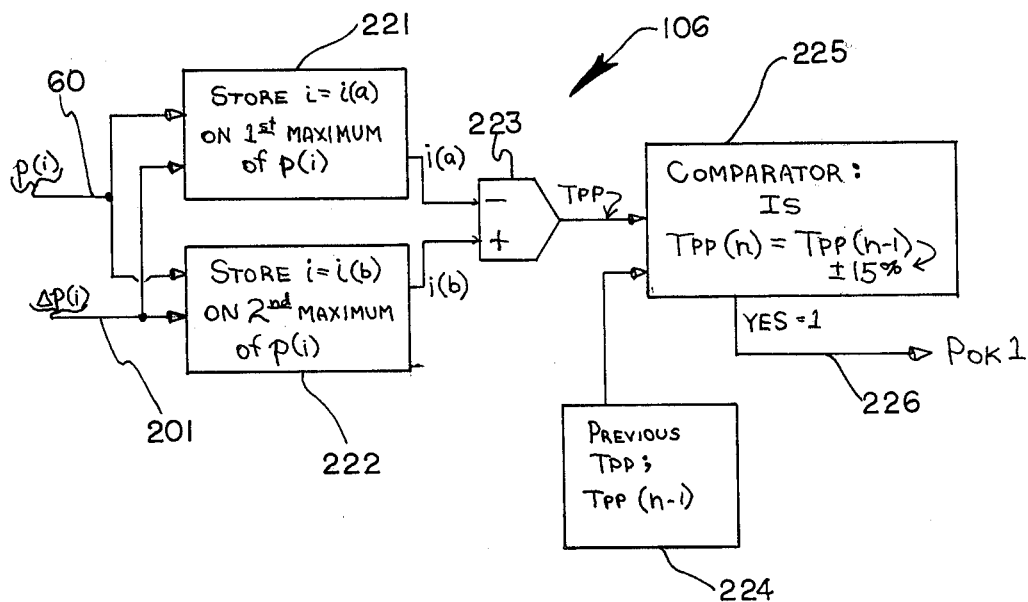
FIG. 7G discloses the circuit operation of the period check of FIG. 6.

An additional artifact detecting circuit 106 tests the heart pulse period (Tpp, 62 of FIG. 4A) of the heart pulse pair and compares it to the previously measured heart pulse pair period during the previous cuff deflation increment interval. This circuit is shown in FIG. 7G. Circuit 221 determines the sample number of the first heart pulse maximum and circuit 222 does the same on the second heart pulse. Subtractor 223 calculates the peak to peak time period Tpp as the difference of these sample clock values. Time period Tpp is then compared in circuit 225 with the previous Tpp 224 and if they are equal within a 15% tolerance, then the test is satisfied. This test is disabled during the first pressure deflation so that the "previous value" may be stored.

The time period checking circuit is a valuable artifact detecting circuit because erroneous arterial pulses which may pass the aforementioned amplitude tests are unlikely to also have precise periodicity.

This relative immunity to artifact is enhanced by several additional criteria which must be met by the pulsations before they are accepted by the device as being true cuff pressure pulsations due to heart action. One criteria is that the rate of pulse rise be within a certain range. That is, if the rate of rise of a pulsation is either too slow (as could be caused by a gentle pressure applied from without or within the cuff) or if the rate of rise is too fast (as could be caused by someone striking the cuff) the pulsation will be disregarded regardless of its amplitude.

Figure 7H:
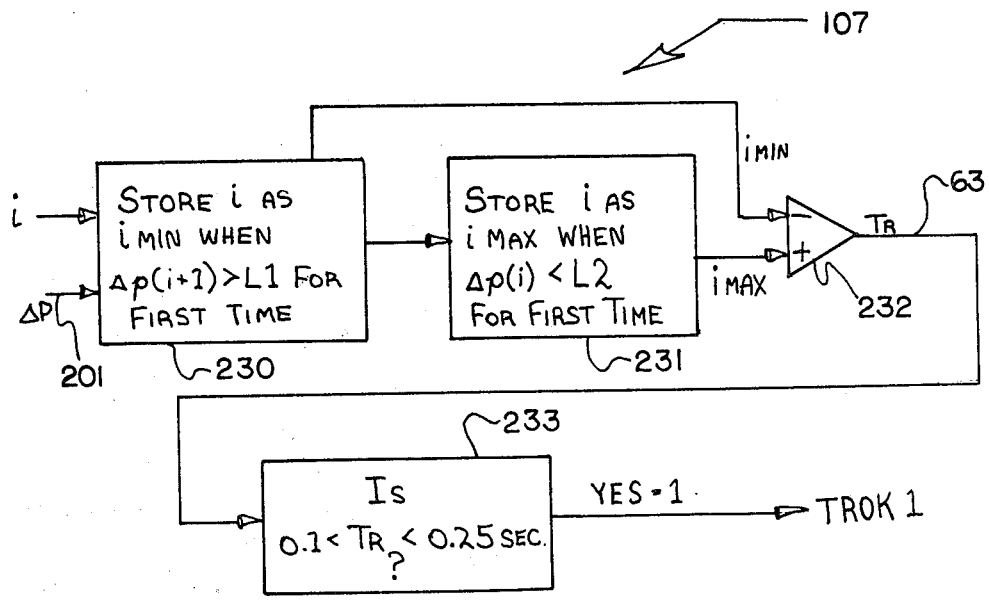
FIG. 7H discloses the circuit operation of the rise time check of FIG. 6.

Such an artifact sensing test is made by circuit 107 by confirming that the heart pulse rise time is within pre-specified limits. FIG. 7H shows that this is accomplished by taking the time difference (expressed as number of sample periods) between the base of the heart pulse and its maximum (see 63 on FIG. 4B). Circuit 230 in FIG. 7H stores the sample clock value, i, where the pressure derivative 201 first exceeds a pre-determined threshold, L1. Circuit 231 similarly stores the "i" value when the derivative is below another threshold (near zero) L2. FIG. 4B shows the relative values of these two thresholds. Circuit 232 determines the rise-time as the difference of the output signal 230 and 231 and circuit 233 compares this rise time value to two predetermined values. If rise time 63 is between these two limits, circuit 233 produces a binary one output signal; otherwise, the output is a zero. This test is valuable at detecting any artifacts which may have periodic, consistent pressure amplitudes, thus passing aforementioned tests, but which are rapidly or very slowly applied to the cuff.

Figure 7I:
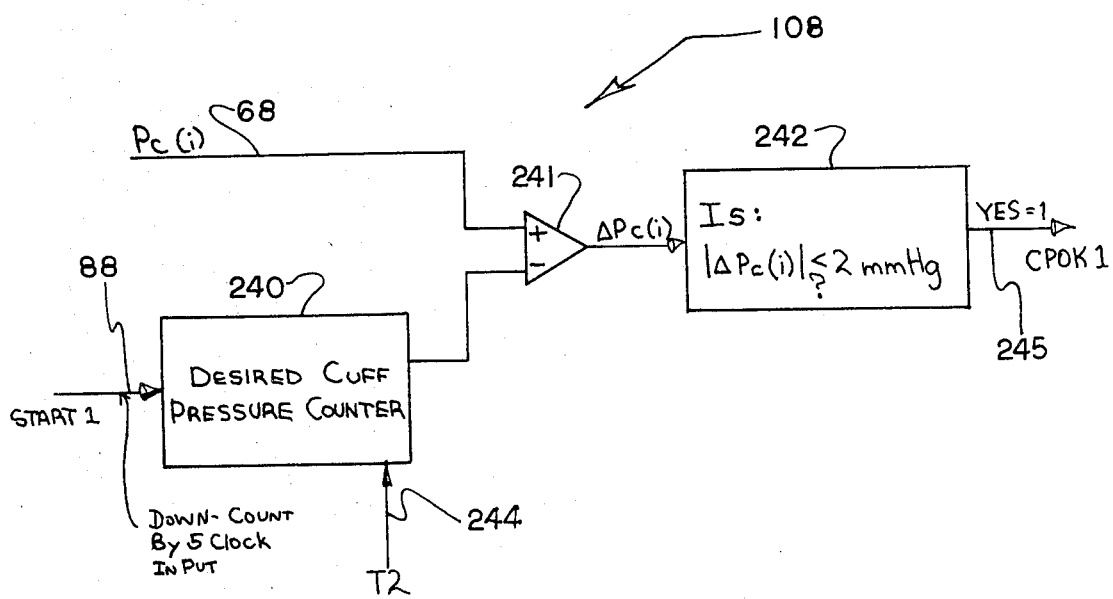
FIG. 7I discloses the circuit operation of the cuff pressure check of FIG. 6.

In order to insure that the mean cuff pressure has not varied significantly during these tests at any given deflation increment, a continuous check is made by circuit 108 and is shown in detail in FIG. 7I. The cuff pressure signal 68 is compared against stored ideal value in counter 240 by subtraction circuit 241 and checks to see that the absolute difference is less than 2 mmHg in circuit 242. If the pressure difference is less than 2 mmHg, then output signal 245 is a binary one; otherwise, it is a zero. When a new cuff deflation increment is requested by "START" signal 88, then the pressure value in counter 240 is decreased by 5 units, preparing circuit 108 for operation at the new cuff pressure. During the pump-up interval, control signal T2 (244) presets register 240 to a value determined by the adaptive pump-up circuit 75.

Figure 9:
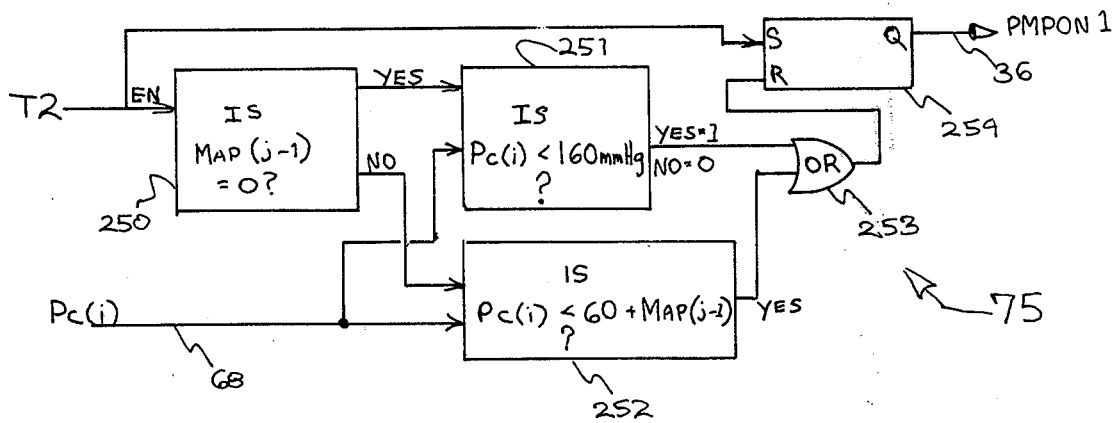
FIG. 9 is a schematic block diagram showing the adaptive pump-up circuit operation of FIG. 5.

FIG. 9 shows the adaptive pump-up circuit in detail as was previously described in FIG. 5. Timing signal T2 activates circuit 250 and sets output latch 254 to a binary one on line 36, which causes the air pump to turn on. If no previous mean arterial pressure measurement has been made (therefore MAP (j−1)=0), then comparator 251 is activated which stops the pump when the cuff pressure 68 has reached 160 mmHg. It does this by outputting a binary one via OR gate 253 to reset the input of latch 254 causing output 36 to be a binary zero. However, should a non-zero, previous MAP exist, then circuit 250 activates comparator 252 which permits the pump to remain on until the cuff pressure 68 exceeds the previous MAP by 60 mmHg, at which time the circuit outputs a binary one via OR gate 253 to reset latch 254 causing the pump to turn off via line 36. This adaptive pump-up circuit provides a plurality of features not found on blood pressure instruments heretofore: (a) patient discomfort is minimized since pressure is not pumped any higher than necessary, (b) the time to deflate is reduced since fewer deflation increments are required reducing patient discomfort; and (c) this circuit alleviates the need for an operator control to set maximum pump-up pressure. During an operation, a patient's blood pressure may change drastically and this circuit will automatically increase or decrease maximum pressure as required.

Since mean pressure is determined by this device by finding the lowest cuff pressure at which the peak to peak oscillations in cuff pressure are maximum it is necessary to measure the amplitude of pulsation at several lower cuff pressures after the supposed maximum oscillation occurs to insure that the higher cuff pressure maximum is the true maximum and not an early false maximum.

Figure 8:
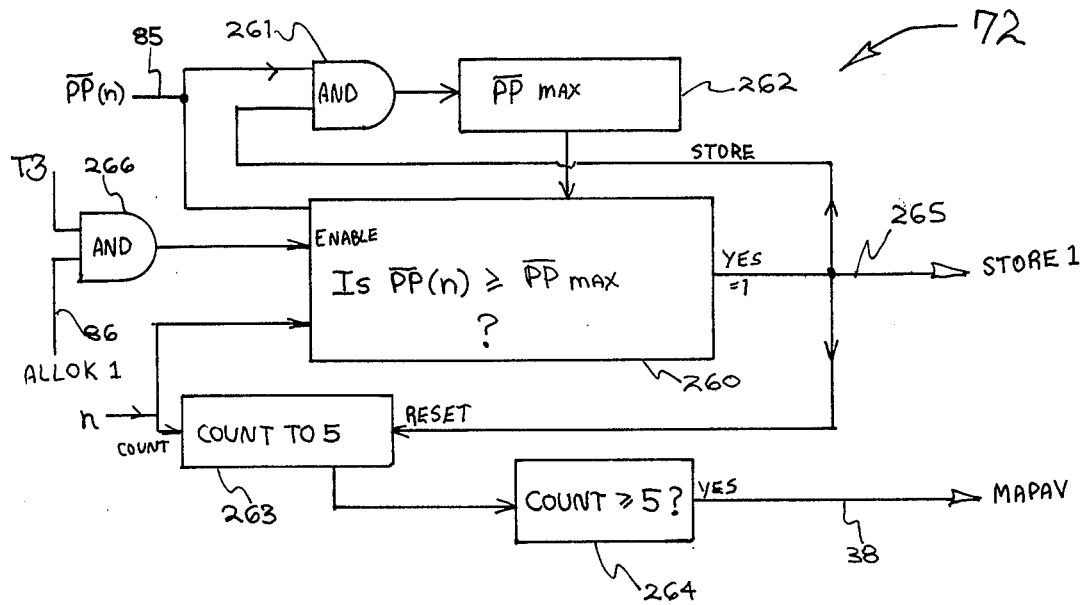
FIG. 8 is a block diagram of the maximum peak-to-peak selector circuit operation of FIG. 5.

The maximum peak to peak selection logic circuits described earlier with FIG. 5 is shown in more detail in FIG. 8. This is a common circuit for saving the maximum of a sequence of numbers presented to it with the addition of a count to five timer to terminate the operation five cuff deflation increments after a maximum has been found. In initial operation the register 262 is set to zero. When signal 86 is a binary one (T3=1 during measurement mode), then comparator 260 compares the value in register 262 with the input average peak to peak value 85. If the input signal value is larger, then comparator output signal 265 enables AND gate 261 to input this new higher value into 262. Signal 265 also resets counter 263 to a value of zero. With each new average peak to peak value input signal, counter 263 is upcounted by clock pulse "n". Should no new maximums be found, after five successive values have been tested to the contents of 262, then it is assumed that register 262 contains the last maximum arterial average pulsation. Gate 264 senses that the count is five in 263 and transmits a binary one output signal on MAPAV signal line 38. In this regard it is important to recall that the STORE signal line 265 has caused the corresponding cuff pressure to be stored in register 73 (FIG. 5).

A problem in any electronic pressure sensing means utilizing a pressure transducer is that the zero point of the transducer changes with temperature. This could mean that with no pressure in the cuff, the pressure transducer would have a certain output, which would be different for different temperatures. The problem is that to set the zero point one must specify at what temperature the transducer is. Thus, when the device has warmed up, the zero point is set for zero pressure in the cuff with the transducer having an output corresponding to zero pressure. When the device is first turned on the zero point may be considerably different, (roughly 15 to 20 mm of mercury) that at a later time when the device warms up.

In order to overcome this variability of zero point with varying temperature the present device has an automatic zeroing function which works in the following manner.

Figure 10:
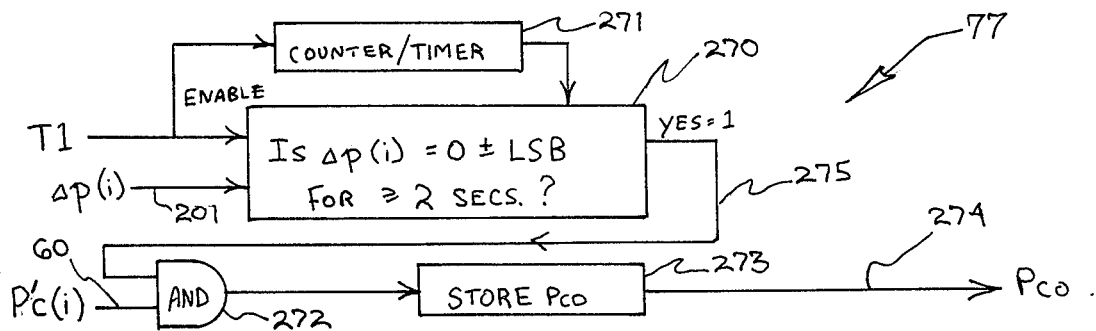
FIG. 10 is a schematic block diagram of the autozero pressure circuit operation of FIG. 5.

The auto-zero pressure circuit 77, shown in detail in FIG. 10 permits long term zero drifts of the pressure transducer to be effectively cancelled out, thus assuring apparatus integrity without additional operator adjustments. This circuit is activated during the pre-measurement interval by timing signal T1 which activates the two second timer 271 and comparator 270. Circuit 270 outputs a binary one on line 275 if the pressure derivative 201 does not vary by more than one least significant digit of the zero digital value during the two seconds that timer 271 activate the circuit. The activation signal on line 275 causes cuff pressure value 60 input signal to be transmitted to register 273. This value is later transmitted by an output signal on line 274 to substractor 71 of FIG. 5. Comparator 270 and timer 271 insure that the deflated cuff is not being moved or otherwise disturbed, thus invalidating the true zero value.

As noted above, every time the apparatus measures the peak to peak value it also measures the pressure which existed in the cuff at that time. The apparatus measures first the peak to peak value of the oscillation and then it switches internally and measures the value of the pressure in the cuff itself which is the absolute value of the pressure such as 98, 100 or 150 millimeters of mercury.

The cuff is emptied at the end of 5 cycles after it completely measures the average maximum peak to peak oscillation. The cuff is emptied quickly once the mean blood pressure has been determined since discomfort to the patient would occur if the pressure were slowly decreased. The rationale for continuing the determination several cycles after the maximum peak to peak value is obtained is to be sure that the maximum obtained wasn't a premature maximum.

When first used, the apparatus initially pumps up the pressure in the cuff to approximately 160 millimeters of mercury. However, on succeeding determinations the cuff is inflated approximately 60 mm Hg over the previously determined mean pressure. Thus, if the mean pressure is 80, the cuff would be inflated to 140 mm Hg the next time.

Thus the automatic apparatus pumps up the cuff each time to the proper pressure and measures the mean arterial pressure without a transducer or other mechanism external to the cabinet. This construction makes the apparatus very rugged and easy to make.

This construction allows the operator to more accurately measure indirect blood pressure, because the operator is not constrained by the time it takes to inflate and deflate the cuff. The cuff is deflated on the basis of how good the data is. Therefore, the apparatus can hold at one particular pressure until acceptable pulsation data is obtained whereas on a constantly deflating machine, it is possible to obtain an incorrect or an inaccurate reading at a particular deflation due to an irregularity which is kept as a valid value by the machine.

In essence what the apparatus does is that it is looking for two (or three) successive peaks which are very close togather in peak to peak value and which additionally do not have too fast or too slow a rise time or which do not have too long a duration. That is, the pulse fluctuation has to take place in the proper amount of time and must perform in the same manner as a real arterial pulse. Even if the pulses were the right size, for example, two pulsations occurred which were the right size, very close together but which went up very slowly and came down very slowly, the apparatus would reject the pulsations and say that these pulsations were not arterial pulses (i.e. perhaps someone must have bumped the cuff twice and it was bumped the same way both times, but it wasn't bumped like an arterial heartbeat). So the apparatus not only can reject pulses when their peak to peak value is of a non-acceptable tolerance, it can reject pulses through their shape i.e. how fast or how slow they reach their peak. The apparatus can only make all of these decisions by being able to hold at each pressure for a variable length of time until it gets good data. The time of holding however, does not extend beyond 14 to 16 heartbeats, or a predetermined amount of time in which case the fail safe timer 32 sounds the alarm 29–31.

The circuits described are all readily implemented with commercially available electronic components as previously mentioned and FIG. 11 shows a portion of the circuitry, functionally described in FIG. 1, in detail with integrated circuit type numbers shown which are familiar to those skilled in the art.

In an additional embodiment, instead of storing the pressure readings internally a small accessory printer (not shown) can be plugged into the rear of the cabinet and each pressure as it is determined by the device will be digitally printed on a paper tape much like an adding machine prints numbers on a paper tape. In this way a hard copy record of the entire blood pressure history of the patient can be obtained without operator intervention or effort. This hard copy record recorded by the device itself is useful in research and for later review.

While the preferred embodiment of the invention has been disclosed, it is understood that the invention is not limited to such an embodiment since it may be otherwise embodied in the scope of the appended claims.

What is claimed is:

1. Apparatus for producing information indicative of the mean blood pressure of a living subject through indirect measurement comprising:
   (a) inflatable, deflatable cuff means;
   (b) pump means, connected to said cuff means, for inflating said cuff to a pressure above systolic pressure of said subject;
   (c) deflating means, connected to said cuff means, for controlled deflation of said cuff means;
   (d) means for measuring cuff pressure and, at a given cuff pressure, pressure pulsations in said cuff means caused by heartbeats of said subject;
   (e) control means, responsive to said means for measuring, for initially energizing said pump means to inflate said cuff, and for subsequently energizing said deflating means incrementally to deflate said cuff at predetermined pressure increments;
   (f) wherein said measuring means includes:
      (i) means for detecting, for each successive set of said pulsations occasioned by successive heartbeats, pulsation amplitude and pulsation time rate of change,
      (ii) means for identifying, at each of said cuff pressure increments, the occurrence of at least two successive sets of pulsations which meet predetermined amplitude and time rate of change criteria relative to one another,
      (iii) means, responsive to said means for identifying, for energizing said control means to deflate said cuff by an increment upon identification of said occurrence of pulsations within said criteria, and
      (iv) means, responsive to said means for identifying, for comparing specified peak to peak amplitude factors of identified pulsations at successive cuff pressure increments; and (g) output means, responsive to said means for comparing, for indicating mean blood pressure as the lowest cuff pressure increment corresponding to the largest of said specified peak-to-peak amplitude factors.

2. An apparatus in accordance with claim 1 and further including adjustable means for storing an upper limit and a lower limit for said mean arterial pressure, means for comparing said upper limit and said lower limit with the mean arterial pressure indicated by said output means, and alarm means responsive to said comparing means for indicating occurrence of a measured mean arterial pressure above said upper or below said lower limit.

3. An apparatus in accordance with claim 1 including means responsive to said means for measuring for fully deflating said cuff means when said cuff pressure has been reduced below a predetermined minimum.

4. An apparatus in accordance with claim 3 and further including counter means, responsive to said means for measuring, for energizing said means for deflating after a predetermined number of cuff pressure increments following the measurement of said maximum peak-to-peak average value.

5. An apparatus in accordance with claim 3 and further including adjustable time delay means for restarting the apparatus a predetermined time after the most recent indication by said output means.

6. An apparatus in accordance with claim 3 including means for counting the number of pressure pulsation signals occurring at each of said pressure increments and for fully deflating said cuff means when the number of pressure pulsation signals at said increment is in excess of a predetermined maximum.

7. An apparatus in accordance with claim 1 including an overpressure switch connected to said cuff means for actuating said deflating means to fully deflate said cuff means when said cuff pressure is in excess of a predetermined maximum.

8. An apparatus in accordance with claim 1 wherein said measuring means includes a pressure transducer responsive to the pressure in said cuff means to produce an output voltage signal representative of said cuff pressure and said pressure pulsations.

9. An apparatus in accordance with claim 1 wherein said means for detecting includes means for isolating fluctuating signal components from d.c. signal components of said pulsations, and means for selectively processing said components in digital fashion.

10. Apparatus as described in claim 1 wherein:
(a) said means for detecting includes means for evaluating the time derivative of said pulsations;
(b) said means for identifying includes:
  (i) means for comparing said time derivative with a predetermined threshold,
  (ii) means for detecting the pulsation peak next after said derivative exceeds said threshold,
  (iii) means for comparing successive ones of said detected pulsation peaks; and
(c) said means for identifying includes means for averaging successive said peaks which are within predetermined differentials of each other, to produce an average peak value defining said amplitude factor.

11. Apparatus for producing information indicative of the mean blood pressure of a living subject through indirect measurement comprising:
(a) inflatable, deflatable cuff means;
(b) pump means, connected to said cuff means, for inflating said cuff to a pressure above systolic pressure of said subject;
(c) deflating means, connected to said cuff means, for controlled deflation of said cuff means;
(d) means for measuring cuff pressure and, at a given cuff pressure, pressure pulsations in said cuff means caused by heartbeats of said subject;
(e) control means, responsive to said means for measuring, for initially energizing said pump means to inflate said cuff, and for subsequently energizing said deflating means incrementally to deflate said cuff at predetermined pressure increments;
(f) wherein said measuring means includes:
  (i) means for detecting, for each successive set of said pulsations occasioned by successive heartbeats, pulsation amplitude,
  (ii) means for identifying, at each of said cuff pressure increments, the occurrence of at least two successive sets of pulsations which meet predetermined amplitude criteria relative to one another,
  (iii) means, responsive to said means for identifying, for energizing said control means to deflate said cuff by an increment upon identification of said occurrence of pulsations within said criteria, and
  (iv) means, responsive to said means for identifying, for comparing specified peak-to-peak amplitude factors of identified pulsations at successive cuff pressure increments; and
(g) output means, responsive to said means for comparing, for indicating mean blood pressure as the lowest cuff pressure increment corresponding to the largest of said specified peak-to-peak amplitude factors.

* * * * *